(12) United States Patent
Clair et al.

(10) Patent No.: US 10,091,900 B2
(45) Date of Patent: Oct. 2, 2018

(54) FEEDTHROUGH CONNECTORS

(71) Applicant: Oticon Medical A/S, Smørum (DK)

(72) Inventors: Pierre-Yves Clair, Smørum (DK); Hervé Ibanez, Smørum (DK); Frederic Bessoule, Smørum (DK); Adrien Thomas, Smørum (DK)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 15/196,330

(22) Filed: Jun. 29, 2016

(65) Prior Publication Data

US 2017/0006724 A1 Jan. 5, 2017

(30) Foreign Application Priority Data

Jun. 30, 2015 (EP) ..................................... 15174692

(51) Int. Cl.

| | |
|---|---|
| *A61N 1/375* | (2006.01) |
| *A61N 1/36* | (2006.01) |
| *H05K 5/06* | (2006.01) |
| *H02G 3/22* | (2006.01) |
| *H05K 5/02* | (2006.01) |
| *H05K 5/03* | (2006.01) |
| *A61N 1/362* | (2006.01) |

(52) U.S. Cl.
CPC ............... *H05K 5/069* (2013.01); *A61N 1/36* (2013.01); *A61N 1/36036* (2017.08); *A61N 1/3754* (2013.01); *H02G 3/22* (2013.01); *H05K 5/0247* (2013.01); *H05K 5/03* (2013.01); *A61N 1/362* (2013.01); *A61N 1/3605* (2013.01)

(58) Field of Classification Search
CPC ..... H05K 7/00; A61N 1/36032; A61N 1/3754
USPC ......................................................... 361/728
See application file for complete search history.

(56) References Cited

U.S. PATENT DOCUMENTS

| | | | |
|---|---|---|---|
| 7,630,768 | B1 | 12/2009 | Coffed et al. |
| 2004/0257884 | A1 | 12/2004 | Dalton et al. |
| 2013/0070423 | A1 | 3/2013 | Iyer et al. |
| 2014/0049924 | A1 | 2/2014 | Deininger et al. |

*Primary Examiner* — Carl H Layno
*Assistant Examiner* — John Eric C Morales
(74) *Attorney, Agent, or Firm* — Birch, Stewart, Kolasch & Birch, LLP

(57) ABSTRACT

According to an embodiment, an implantable medical device is disclosed. The device includes a sealed housing enclosing an electronic circuitry, a plurality of feedthrough conductors, each conductor of the plurality of feedthrough conductors includes a proximal end part connected to the enclosed electronic circuitry and a distal end part available external to the housing. The device further includes a plurality of spatially separated feedthrough connectors configured to provide terminal connections, away from the plurality of feedthrough conductors, for a plurality of electrical wires. Each connector of the plurality of spatially separated feedthrough connectors includes a first end section adapted to be connected with the distal end part of a feedthrough conductor of the plurality of feedthrough conductors and a second end section adapted to be connected with one of the plurality of electrical wires.

17 Claims, 8 Drawing Sheets

FEEDTHROUGH CONNECTORS

FIELD

The disclosure relates to implantable medical devices. In particular, the disclosure relates to a feedthrough connector for the implantable devices like a cochlear implant, heart pacemakers, or a brain stimulating device. The feedthrough connector provides a terminal connection, away from a feedthrough, for an electrical wire that has sensing and/or stimulating electrode at a wire end distal from the terminal connection. The electrodes are implanted in a tissue targeted for stimulating a bodily part such as cochlea, heart muscle, particular area of brain, etc.

BACKGROUND

Implanted medical devices utilize hermetically sealed housing to isolate the device from the body environment. Such devices require that electrical signals to be passed from within the housing to external connectors or vice-versa while maintaining hermeticity of the housing. Depending upon the configuration of the implantable device, there may be multiple electrical paths required between an electronic circuitry enclosed within the housing and the external connectors. These paths are usually electrically and mechanically integrated with the device in order to provide a safe, long-term arrangement that does not compromise hermetic housing.

The implantable medical device may include an implanted part of cochlear implant system.

Many implantable devices use feedthroughs to connect the hermetically housed electronic circuitry with implanted measuring and/or stimulating electrode and/or electromechanical actuator. However, the desirability of making the implanted medical devices smaller and/or less obtrusive raises design challenges, particularly in relation to the connecting a number of closely concentrated feedthroughs to respective wires outside the housing.

Conventionally, an operator directly welds each wire to feedthrough pin manually. The operator makes a little pearl at an edge of the wire using a torch flame. Thereafter, the operator electrically welds the pearl to the feedthrough pin with a tweezers connected to an impulse generator. Apart from operator dexterity, this implementation requires enough clearance between two neighboring feedthroughs to prevent reflection damage and weld interference. Therefore, securing a reliable weld connection between the wire and the feedthrough pin is extremely difficult when the feedthroughs that are closely concentrated in a small area.

Furthermore, there might be a risk of contact between closely welded weld-connections at neighboring feedthroughs and/or very poor yield, which is usually due to the rework required if the first welding attempt is not correct. Therefore, the classical hand wire welding and wire-by-wire welding between the closely concentrated feedthrough pins and the wire is not feasible. Also, with an increasing number of required electrical paths, there is an excess amount of the wires present in proximity to feedthroughs, and orienting the excess wires as these wires exit the medical device while maintaining the relatively small profile is also challenging.

Therefore, there is a need to provide a solution that addresses at least some of the above-mentioned problems.

SUMMARY

According to an embodiment, an implantable medical device is disclosed. The device includes a sealed housing that encloses an electronic circuitry and a plurality of feedthrough conductors. Each conductor of the plurality of feedthrough conductors includes a proximal end part connected to the enclosed electronic circuitry and a distal end part available external to the housing. The device further includes a plurality of spatially separated feedthrough connectors configured to provide terminal connections, away from the plurality of feedthrough conductors, for a plurality of electrical wires. Each connector of the plurality of spatially separated feedthrough connectors includes a first end section adapted to be connected with the distal end part of a feedthrough conductor of the plurality of feedthrough conductors and a second end section adapted to be connected with one of the plurality of electrical wires.

The implantable medical device may include an implanted part of cochlear implant system.

According to an embodiment, a cochlear implant comprising the disclosed implantable medical device comprising the implantable part is also part of this disclosure.

The term feedthrough conductors refer to the provision of an electrically conducting path extending from one side of the housing to another. The electrically conducting path extends from interior of a hermetically sealed housing, to an external location outside the housing. This arrangement allows one or more electrical connections to be made with electronic circuitry or components within the hermetically sealed housing, whilst protecting the circuitry or components from any damage or malfunction that may result from exposure to the environment surrounding the housing.

Providing connection distal from the feedthrough conductors allows for making wire connections such as weld connections away from the feedthrough conductors. This is particularly useful for securing a reliable connection (e.g. weld connection) between the wire and the feedthrough when the feedthroughs are closely concentrated in a small area. Thus, challenges like reflection damages and weld interference relating to clearance between two neighboring feedthroughs are avoided or substantially reduced.

As an illustration, one can visualize the plurality of connectors as fingers of a spread human hand—section proximal to finger tip is made available as the second end section of the connector for providing connection such as welding wire to the second end section and feedthroughs being provided proximal to finger connecting section (at the web) of the hand. With this arrangement, the feedthrough connectors moves connection site (e.g. weld connection sites) to an area of low stress, thereby facilitating securely connecting like by welding electrode array wire at the peripheral extremity of the housing, thus connecting to concentrated configuration of thin feedthrough conductors.

In an embodiment, the plurality of spatially separated connectors are positioned onto a non-conductive unit. The plurality of spatially separated connectors are configured such that a first distance between first end sections of at least one pair of neighboring feedthrough connectors is less than a second distance between second end sections of the at least one pair of neighboring feedthrough connectors.

The second distance is along a circumferential length of the non-conductive unit, thereby allowing for increasing the second distance compared to the first distance. This allows for providing a greater clearance between connection sites like welding sites, when connections with the electrical wires are made. Having the second distance along the circumferential length also allows for more flexibility in increasing the second distance between the connection sites. This may be accomplished by an illustrative embodiment, where the primary section of at least one connector of the plurality of feedthrough connectors includes at least one turn along a length of the primary section.

In another embodiment, a first surface area of the first end section is less than a second surface area of the second end section. Having a relatively smaller first surface area allows for securely fixing the feedthrough conductors in the feedthrough connectors even when the feedthrough conductors are densely packed in a small area, whereas having a relatively larger second surface area allows for providing a large area for securely connecting the wires such as by welding to the second end section.

In an embodiment, a combination of higher distance between the second end sections because of increased clearance for connection (e.g. for welding) and a relatively larger second surface area provides enough clearance and a larger connection area for providing a secured connection such as weld connection between the wire and the electrical connector, and electrical coupling of the wires with the feedthrough conductors.

In an embodiment, each connector of the plurality of spatially separated feedthrough connectors includes a bend around a peripheral edge of the non-conductive unit. The bend lies between the first end section and the second end section of the connector and the bend defines a primary section comprising the first end section and a secondary section comprising the second end section of the feedthrough connector. In an embodiment, the primary section of at least one connector of the plurality of feedthrough connectors includes at least one turn along a length of the primary section. Inclusion of turns allows for changing the second distance, thereby increasing the clearance between neighboring second end sections.

In an embodiment, the non-conductive unit rests on the housing. The unit may rest on the side of the housing where the feedthrough conductors are made accessible external to the housing. The non-conductive unit is adapted to support the plurality of spatially separated feedthrough connectors and to isolate a pair of neighboring feedthrough connectors of the plurality of spatially separated feedthrough connectors. Thus, the feedthrough connectors are both mechanically and electrically isolated in order keep their electrical paths isolated from one other.

In an embodiment, the non-conductive unit includes a base on which at least a part of the primary section of the connector rests, the peripheral edge along which the bend rests, and a side section to which the secondary section abuts. It might be possible to have the feedthrough connectors where such bend is not made and the secondary section also either rests on the base of the non-conductive base or protrudes slightly outside the periphery of the non-conductive unit. However, in order to keep the profile of the device small and to provide mechanical stability to the feedthrough connectors along with ease of providing connection such as by welding, such bend may be provided.

In an embodiment, the non-conductive unit includes a plurality of guiding grooves. Each groove of the plurality of guiding groove is adapted to receive the connector of the plurality of spatially separated feedthrough connectors. This allows for isolating a pair of neighboring feedthrough connectors of the plurality of spatially separated feedthrough connectors. The guiding grooves reflect the structure, for example turns in the primary section, of the feedthrough connectors. In addition to providing isolation between electrical paths for the feedthrough conductors, the grooves may also ensure that the feedthrough connectors are positioned correctly and do not slide around over the base of the non-conductive unit.

In an embodiment, a hole at the first end section of the connector is provided. The hole is configured to receive the feedthrough conductor. The internal dimension of the hole is made such that the hole is adapted to securely receive the feedthrough conductors. For example, the feedthrough conductors may snap fit into the hole or may employ other implementation facilitating fitting the feedthrough conductors into the hole with relatively easy operation. Thus, the conventional challenges of connecting wires to feedthrough conductors such as by welding in densely packed feedthrough conductors is avoided.

In another embodiment, a connection to connect the wire to the second end section of the feedthrough connector is provided. The connection is distal to the plurality of feedthrough conductors. The connection may include weld connection between the wire and the second end section. Like earlier, the conventional requirement of connecting, say by a welding process, in densely packed feedthrough conductors and related challenges is eliminated or at least substantially avoided.

In an embodiment, at least one wire of the plurality of electrical wires includes an extra wire length typically in form of at least one wire loop in immediate proximity to a connection site (such as welding site) at the second end section. Additionally, each wire of the plurality of electrical wires is provided with the extra wire length. The extra wire length allows for reworking on the connection using the extra wire length, if earlier attempts to make a satisfactory connection like weld connection fail. With this, the manufacturing yield of the implantable medical device is kept high.

A pair of insulating members may also be provided. The insulating members are configured to sandwich the extra wire length therebetween. Sandwiching the extra length between the neighboring insulating members allow for isolating the electrical paths of wires connected to the neighboring second end sections. In addition, the insulating members may support the wire before the connection such as weld connection with the second end section is made.

According to an embodiment, the insulating member extends beyond the peripherial edge of the non-conductive unit. In different implementations, the insulating member is an integral part of the non-conductive unit or the insulating member may also be configured to removably attach to the non-conductive unit. In order to provide a removably attachable insulating member, the non-conductive unit and the insulating members include corresponding mating members such as a nut-bolt assembly, a snap-fit assembly, a track assembly along the side section of the unit where the track assembly is adapted to receive complimentary member of the insulating member, etc. Other implementations conceivable by the skilled person are also within the scope of the disclosure.

The extra wire length protects device from traction and flexion solicitations during manufacturing, and/or use. The extra wire length avoids having a direct traction and/or flexion stress on the connections (such as weld connections) by transferring the stress on insulating members and the non-conductive unit. During manufacturing or device use, the soft transition area by way of connecting electrical wires, along with insulation members and the non-conductive unit allow for these components to move together. This construction also offers absorption and dissipation of the energy in the soft material used for making the insulation members and/or non-conductive unit, without breakage of connection and/or wire in events of impact on the housing or the connector. The implementation is thus adapted to little movements and efforts on array and eliminates or substantially reduces direct stresses on the connection, thus increasing reliability of the implant. It is conceivable to provide the extra wire length by way of one, two or more wire loops. However, providing a higher number of loops may depend upon cost considerations and time availability.

In an embodiment, a peripheral cover including a cover section is provided. The cover section co-operates with a unit section of the non-conductive unit to define a wire path and/or a wire entry/exit port when the peripheral cover is in an assembled position.

In an embodiment, the peripheral cover is adapted to fix to the non-conductive unit, and in the assembled position the peripheral cover covers at least a part of the secondary section, and side section.

In an embodiment, one end of the wire is connected to the feedthrough connector and the runs along a periphery of the non-conductive unit within the wire path and another end of the wire exits the wire entry/exit port. The electrical wires are adapted to run from the corresponding connection site (such as weld site) at the respective second end section of the feedthrough connector through the wire path and exit the entry/exit port.

In different embodiments, the plurality of electrical wires are adapted to run towards the entry/exit port individually or as electrically isolated bunched wires. It is preferred the plurality of wires run within the wire path and exit as bunched wires. The bunched wires include electrically isolated wires originating from individual connection sites (e.g. weld site) and the electrically isolated wires are wrapped around with a single insulating sheath cover.

The wires running towards the entry/exit port may exit within a lead body. The lead body connects the electrode array (not shown) to the enclosed electronic circuit. The plurality of wires, exiting the entry/exit port, passes through the lead body to bring electrical signal from the electronic circuit to the electrode array positioned within the cochlea. The wires that conduct electrical signals are connected to the electrodes within the electrode array. For example, electrical signals which correspond to a low frequency sound may be communicated via a first wire to an electrode near the tip of the electrode array. Electrical signals which correspond to a high frequency sound may be communicated by a second wire to an electrode near the base of the electrode array.

According to one illustrative embodiment, there may be one wire exiting the entry/exit port for each electrode within the electrode array. The electronic circuit may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires and portions of the electrodes are encased in a flexible body. The flexible body may be formed from a variety of biocompatible materials, including, but not limited to medical grade silicone rubber. The flexible body secures and protects the wires and electrodes. The flexible body allows the electrode array to bend and conform to the geometry of the cochlea.

The device may further include an overmoulding adapted to surrounding the feedthrough connector assembly.

The non-conductive unit may be made of biocompatible silicone, or polyurethane. The feedthrough connectors may be made of platinum-iridium, stainless steel. The housing and overmoulding may be made of silicone. The electrical wire may also be made of platinum-iridium with a polyimide insulation. It is apparent that the skilled person may use other suitable materials and such use is within the scope of this disclosure.

The hardness of the non-conductive unit and the peripheral cover is approximately 50 shore. This hardness allows for little movement before welding.

According to an embodiment, a method of providing terminal connections, away from a plurality of feedthrough conductors, for a plurality of electrical wires in an implantable medical device is disclosed. The method includes manufacturing a plurality of feedthrough connectors that includes an arrangement of holes at a first end section. The arrangement represents an arrangement of the plurality of feedthrough conductors of the device. The hole at the first end section of each connector is configured to receive a corresponding feedthrough conductor. The manufactured plurality of feedthrough connectors is positioned over a non-conductive unit. The plurality of feedthrough conductors are received in a corresponding hole of the plurality of feedthrough connectors. Thereafter, one end of a plurality of electrical wires is individually connected to respective second end section of one of the plurality of feedthrough connectors using a connection technique such as weld connection technique.

The plurality of feedthrough connectors may preferably be manufactured using known microject cutting technology. However, other techniques such as electro-erosion wire process but with an access into holes and typically with relatively less proper edges may also be used.

The method may include one or more of the following steps:

In an embodiment, manufacturing step includes manufacturing the plurality of feedthrough connectors such that the plurality of feedthrough connectors are adapted to, when positioned onto a non-conductive unit, include a first distance between first end sections of at least one pair of neighboring feedthrough connectors that is less than a second distance between second end sections of the at least one pair of neighboring feedthrough connectors. Additionally or alternatively, the manufacture step may also include manufacturing the plurality of feedthrough connectors such that a first surface area of the first end section is less than a second surface area of the second end section.

In another embodiment, manufacturing includes manufacturing the plurality of feedthrough connectors interconnected with a strip. The connecting strip is removed after positioning the feedthrough connectors over the non-conductive unit.

Maintaining the strip between the plurality of feedthrough connectors until the feedthrough connectors are placed over the non-conductive unit allows for maintaining the plurality of feedthrough connectors as a complete mask. The strip may be removed by small forceps after the feedthrough connectors are placed over the non-conductive unit.

In an embodiment, the position of the feedthrough connector over the non-conductive unit includes positioning the plurality of feedthrough connectors in a plurality of guiding grooves of the non-conductive unit such that a pair of neighboring feedthrough connectors are isolated from each other.

In another embodiment, prior to connecting the electrical wires to respective second end section, an extra wire length in form of at least one wire loop in immediate proximity to a connection site (e.g. weld connection site) at the second end section is provided. The extra wire length is also sandwiched between a pair of insulating members.

In yet another embodiment, prior to connecting the electrical wires to respective second end section, the plurality of feedthrough connectors are bent around the peripheral edge of the non-conductive unit. The bend defines a primary section and a secondary section for each of the plurality of feedthrough connectors and the connection such as weld connection is made at the secondary section.

In an embodiment, following the connection of the electrical wires to respective second end section, a peripheral cover is fixed onto the non-conductive unit. The peripheral cover in co-operation with the non-conductive unit defines a wire entry/exit port when the peripheral cover is in an assembled position. Other end of the plurality of electrical wires are then drawn out of the entry/exit port.

In different combinable embodiments, the method is adapted to include features of the device described in preceding paragraphs.

According to an embodiment, a cochlear implant comprises the disclosed feedthrough connector. This encompasses the cochlear implant including one or more features of the feedthrough connector.

BRIEF DESCRIPTION OF ACCOMPANYING FIGURES

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other embodiments. These and other embodiments, features and/or technical effect will be apparent from and elucidated with reference to the illustrations described hereinafter in which:

DETAILED DESCRIPTION

Figure 1:
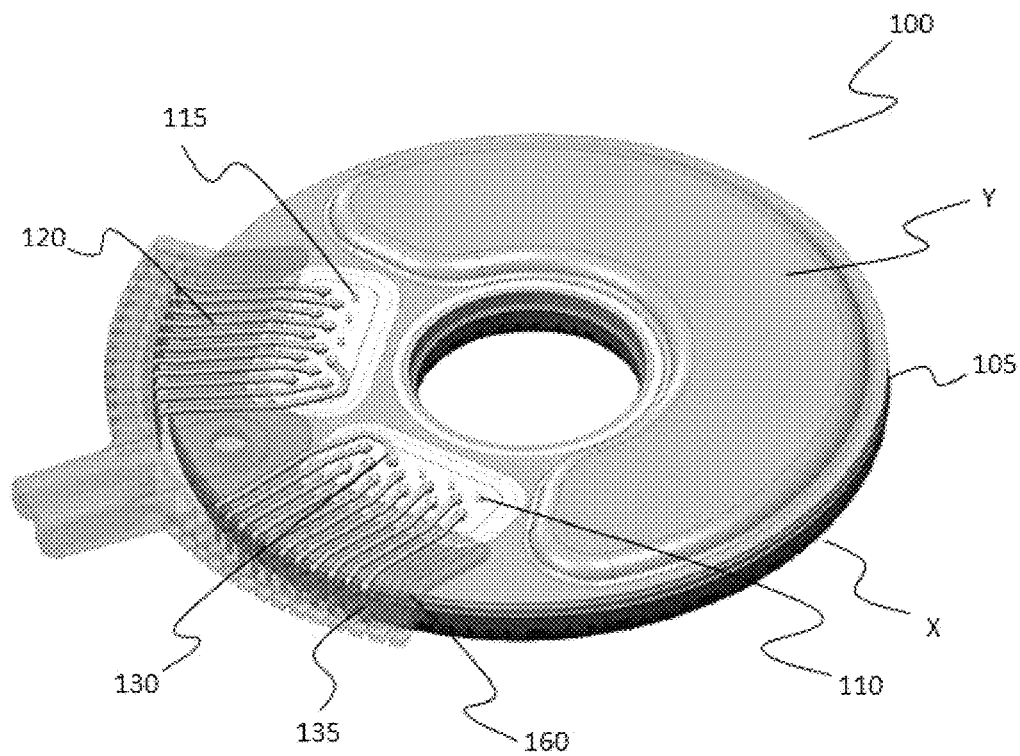
FIG. 1 illustrates an implantable medical device according to an embodiment.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, steps, processes, etc. (collectively referred to as "elements").

The disclosure relates to implantable medical devices. In particular, the disclosure relates to a feedthrough connector for the implantable devices like a cochlear implant, heart pacemakers, or a brain stimulating device.

The cochlear implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part (referred as the implanted medical device) allowing the stimulation to be generated and applied to a number of electrodes (electrode array), which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea. The electrodes are electrically connected to electronics of the implanted device through wires connecting the electrode with feedthrough conductors, which provide an electrical path from interior of a hermetically sealed housing of the implanted device to an external location outside the housing. This arrangement allows one or more electrical connections to be made with electronic circuitry or components within the hermetically sealed housing, whilst protecting the circuitry or components from any damage or malfunction that may result from exposure to the environment surrounding the housing. During operation, the enclosed electronic circuitry receives electrical signals and transmits them down through the feedthrough to the plurality of wires and then to specific electrode contacts of the electrode array. The electrode contacts then generate electrical fields which stimulate the auditory nerve. This provides the patient with a sense of hearing.

Throughout the text, references X and Y refer to two sides of the housing. In the disclosure, for illustrative purposes, the plurality of connectors is resting on a non-conductive unit, which is resting on the Y side of the housing.

Figure 2:
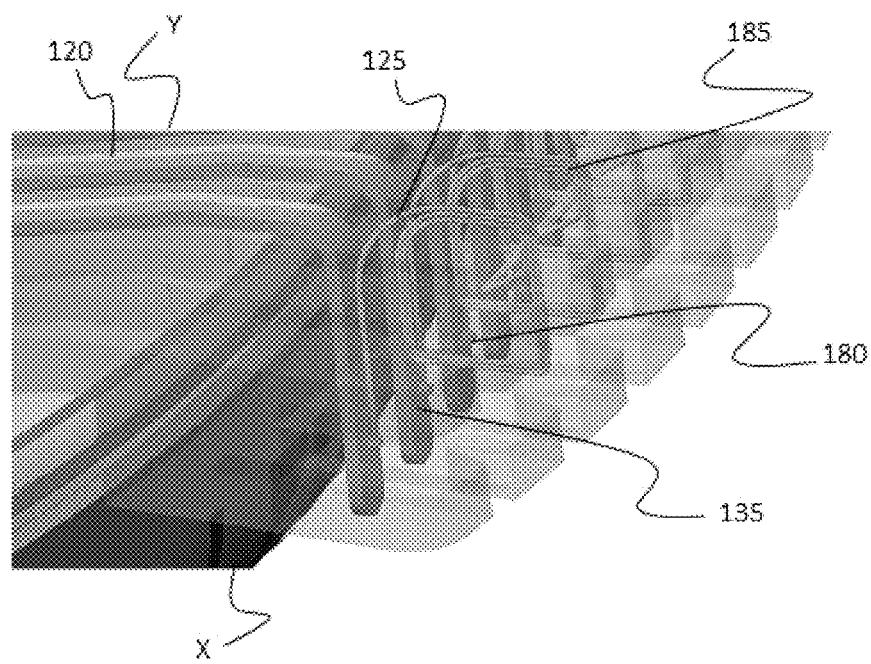
FIG. 2 illustrates an enlarged view of the second end section according to an embodiment.

FIG. 1 illustrates an implantable medical device 100 according to an embodiment and FIG. 2 illustrates an enlarged view of a second end section 135 according to an embodiment. The implantable medical device 100 includes a sealed housing 105 that encloses an electronic circuitry (245, FIG. 5E). A plurality of feedthrough conductors 110 are also provided. Each conductor of the plurality of feedthrough conductors 110 comprising a proximal end part (FIG. 5E, 250) connected to the enclosed electronic circuitry and a distal end part 115 available external to the housing 105. A plurality of spatially separated feedthrough connectors 120 are configured to provide terminal connections for a plurality of electrical wires 125 (FIG. 2). The terminal connection refers to providing a connection site away, preferably proximal to a periphery of the housing, from the plurality of feedthrough conductors 110. Each connector of the plurality of spatially separated feedthrough connectors 120 includes a first end section 130 configured to be connected with the distal end part 115 of a feedthrough conductor of the plurality of feedthrough conductors 110 and a second end section 135 adapted to be connected with one of the plurality of electrical wires 125 (FIG. 2).

In an embodiment, the non-conductive unit 160 rests on the housing 105. The non-conductive unit 160 is configured to support the plurality of spatially separated feedthrough connectors 120 and to isolate a pair of neighboring feedthrough connectors of the plurality of spatially separated feedthrough connectors 120.

In an embodiment, the device further includes a connection 180 such as a weld connection to connect one end of the wire 125 to the second end section 135 of the feedthrough connector 120. The connection 180 is distal from the plurality of feedthrough conductors 110.

Figure 3A:
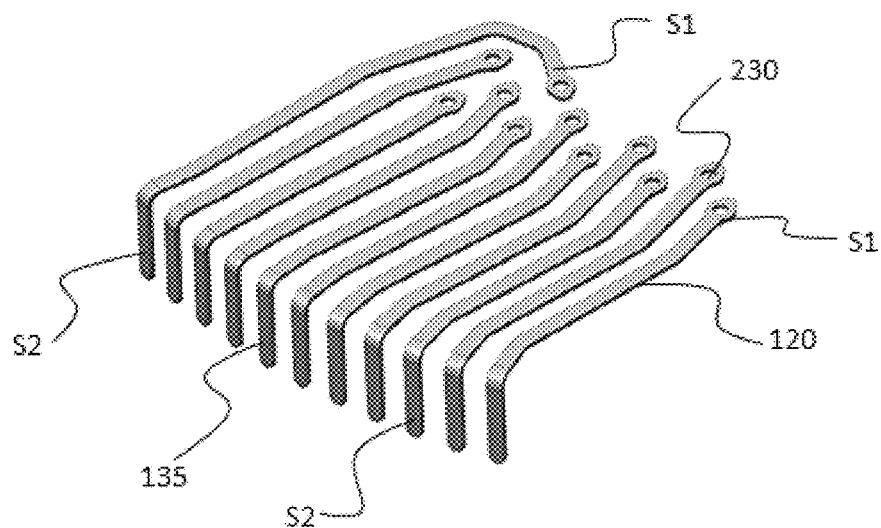
FIG. 3A illustrates a plurality of feedthrough connectors according to an embodiment.

FIG. 3A illustrates a plurality of feedthrough connectors 120 according to an embodiment. Each connector of the plurality of feedthrough connectors 120 include a hole 230 at the first end section 130 of the connector. The hole 230 is configured to receive the feedthrough conductor 110 (as illustrated in FIG. 1).

In another embodiment, the first end section 130 includes a first surface area $S_1$ that is less than a second surface area $S_2$ of the second end section 135.

Figure 3B:
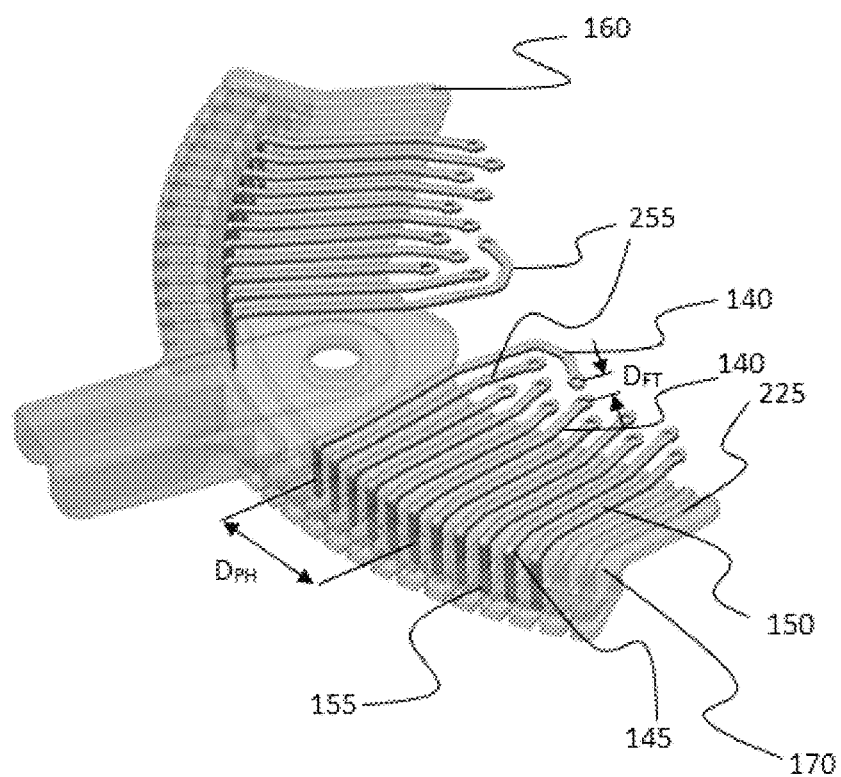
FIG. 3B illustrates the plurality of feedthrough connectors positioned on a non-conductive unit according to an embodiment.

FIG. 3B illustrates the plurality of feedthrough connectors positioned on a non-conductive unit according to an embodiment. The plurality of spatially separated connectors 120, when positioned onto a non-conductive unit 160, are configured such that a first distance $D_{ft}$ between first end sections 130 of at least one pair of neighboring feedthrough connectors 140 is less than a second distance $D_{ph}$ between second end sections 135 of the at least one pair of neighboring feedthrough connectors 140.

In an embodiment, the primary section 150 includes at least one connector of the plurality of feedthrough connectors 120 includes at least one turn 255 along a length of the primary section. Inclusion of turns 255 allows for changing the second distance, thereby the clearance between neighboring second end sections.

In another embodiment, each connector of the plurality of spatially separated feedthrough connectors 120 includes a bend 145 around a peripheral edge 170 of the non-conductive unit 160. The bend is positioned between the first end section 130 and the second end section 135. The bend 145 defines a primary section 150 including the first end section 130 and a secondary section 155 including the second end section 135 of the feedthrough connector.

The non-conductive unit 160 may include a base 165 on which at least a part the primary section 150 rests, the peripheral edge 170 along which the bend 145 rests, and a side section 175 to which the secondary section 155 abuts. (Refer FIG. 5A)

In another embodiment, the non-conductive unit 160 comprises a plurality of guiding grooves 225. Each groove of the plurality of guiding groove is configured to receive the connector of the plurality of spatially separated feedthrough connectors 120. The grooves allow for isolating electrical paths of a pair of neighboring feedthrough connectors of the plurality of spatially separated feedthrough connectors 120.

Figure 4:
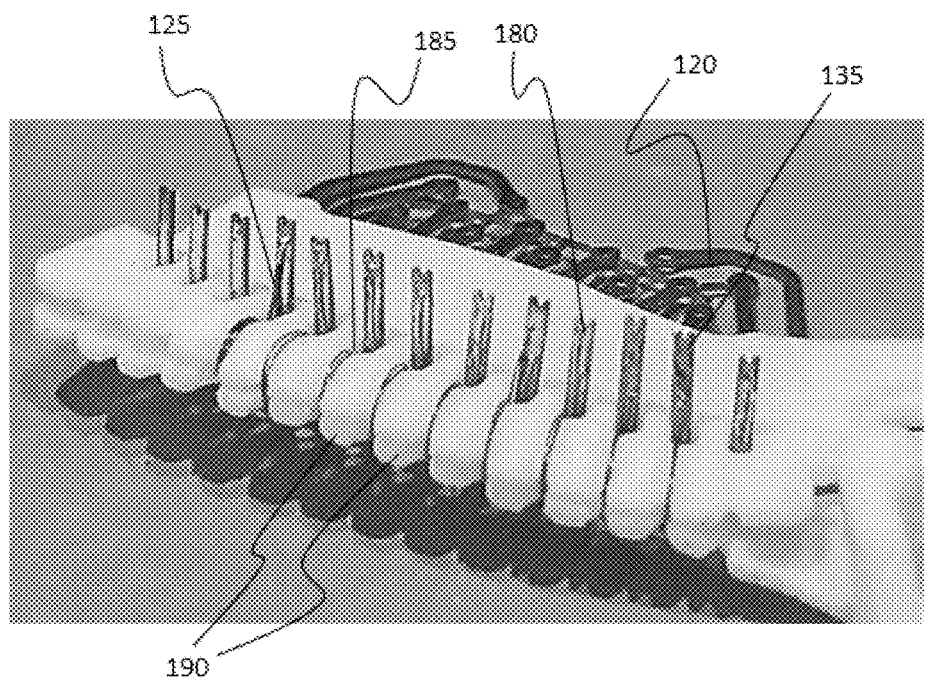
FIG. 4 illustrates an extra wire length and insulation members according to an embodiment.

FIG. 4 illustrates an extra wire length and insulation members according to an embodiment. At least one wire of the plurality of electrical wires 125 comprises an extra wire length 185 in form of at least one wire loop in immediate proximity to a connection site such as a welding site at the second end section 135. Additionally each wire of the plurality of electrical wires is provided with the extra wire length.

The device may further include a pair of insulating members 190. The insulating members are configured to sandwich the extra wire length 185 therebetween. The insulating members 190 extends beyond the peripherial edge 170 of the non-conductive unit 160. In different embodiments, the insulating member 190 may be provided as an integral part of the non-conductive unit 160 or adapted to be removably attached with the non-conductive unit 160.

Figure 5A:
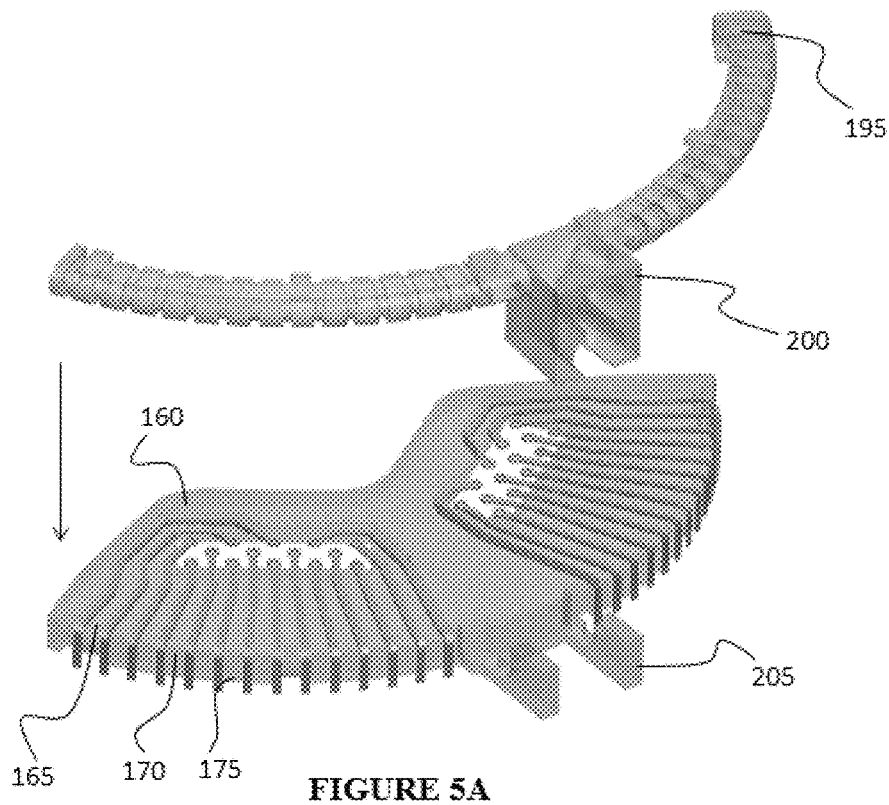
FIG. 5A illustrates a peripheral cover according to an embodiment.

FIG. 5A illustrates a peripheral cover 195 according to an embodiment. The peripheral cover is configured to be fixedly assembled over the non-conductive unit 160. The peripheral cover includes a cover section 200, which in the assembled position is configured to cooperate with a unit section 205 of the non-conductive unit 160 to define a wire path 260 (FIG. 5E) and/or a wire entry/exit port 210 when the peripheral cover 195.

In an embodiment, the peripheral cover 195 is configured to fix to the non-conductive unit 160, and in the assembled position the peripheral cover covers at least a part of the secondary section 155, and side section 175.

Figure 5B:
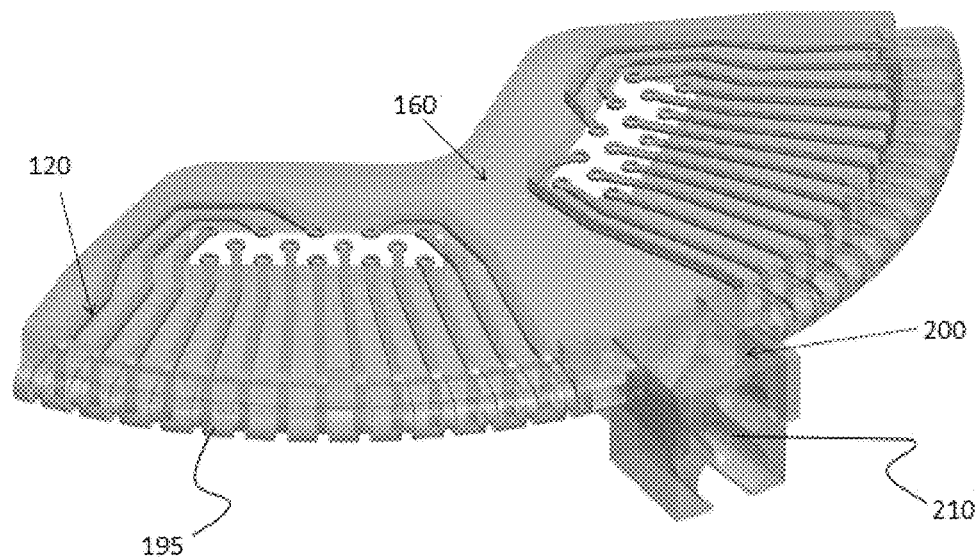
FIG. 5B illustrates a first view of the peripheral cover in an assembled position according to an embodiment.
Figure 5C:
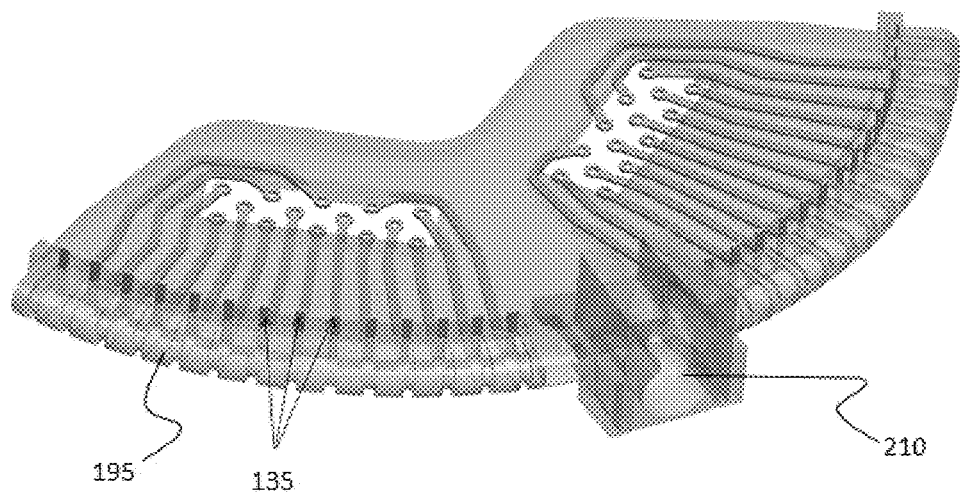
FIG. 5C illustrates a second view of the peripheral cover in the assembled position according to an embodiment.

FIG. 5B illustrates a first view of the peripheral cover 195 in the assembled position over the non-conductive unit 160 according to an embodiment. FIG. 5C illustrates a second view of the peripheral cover 160 in the assembled position over the non-conductive unit 160 according to an embodiment. The first and the second view differ only in the orientation of the non-conductive cover, i.e. in the second view, the assembly of the first view is flipped over.

Figure 5D:
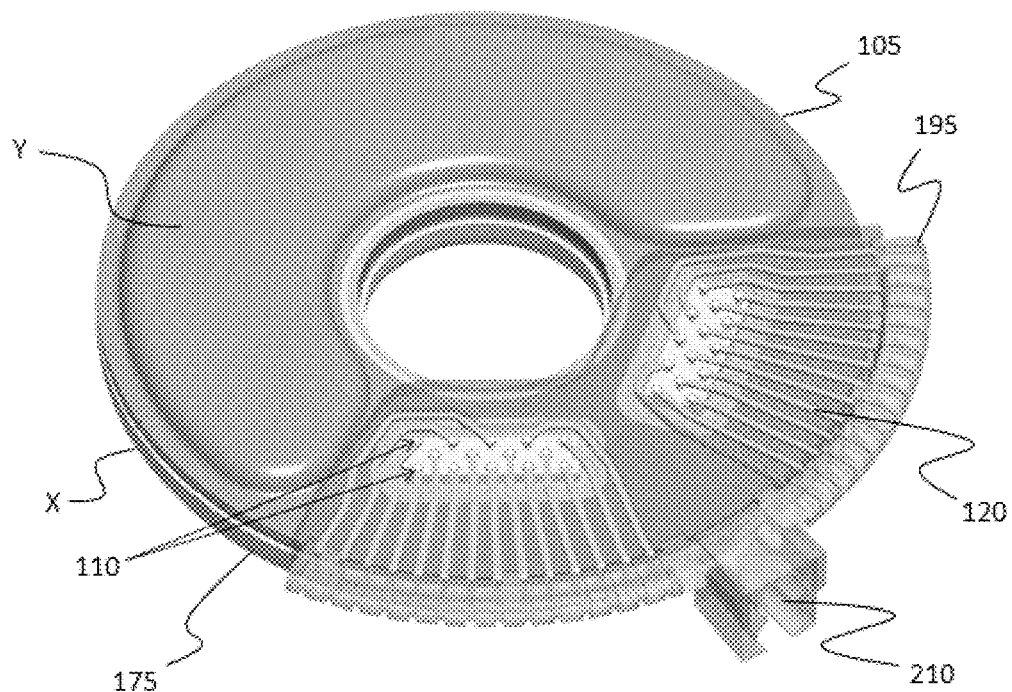
FIG. 5D illustrates the peripheral cover in an assembled position with the non-conductive unit over the housing according to an embodiment.

FIG. 5D illustrates the peripheral cover 160 is in the assembled position over the non-conductive unit 160 and the entire assembly is positioned over the housing 105 according to an embodiment.

Figure 5E:
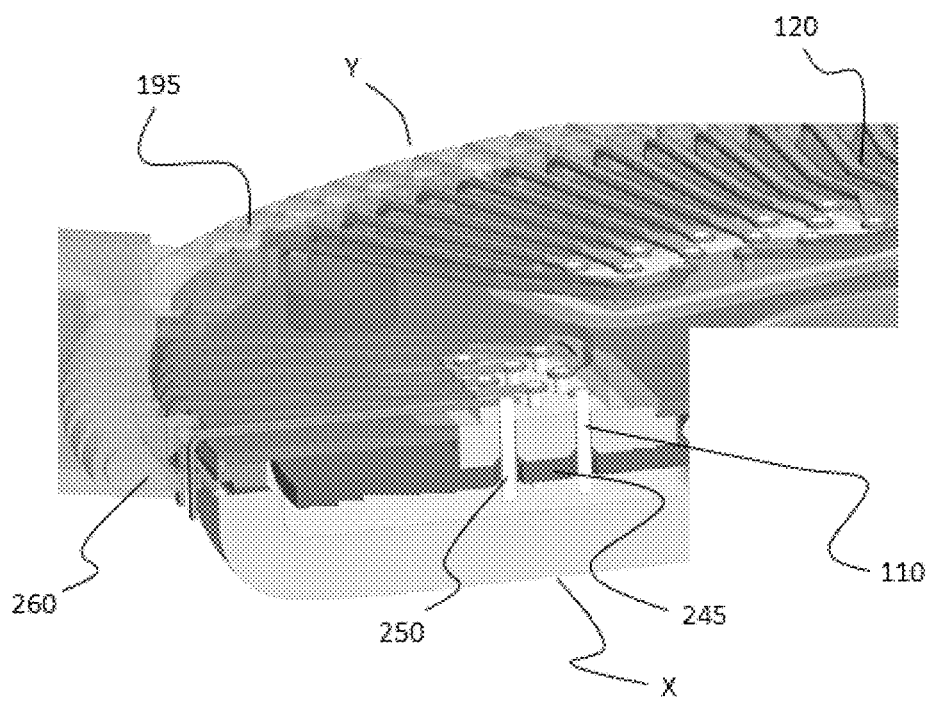
FIG. 5E illustrates a sectionalized view of the implant device according to an embodiment.

FIG. 5E illustrates a sectionalized view of the implant device according to an embodiment. The figure shows internal components of the housing including the electronic circuitry 245 and the proximal end part 250 of the feedthrough conductor connected to the enclosed electronic circuitry. In addition, the figure also shows the wire path 260.

Figure 6A:
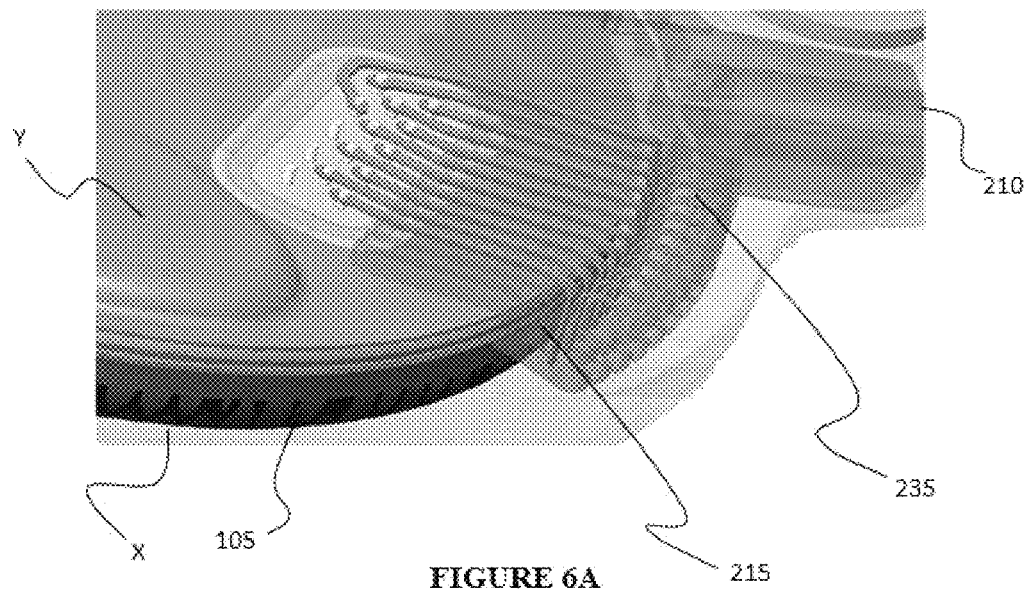
FIG. 6A illustrates wire exiting an entry/exit port according to an embodiment.
Figure 6B:
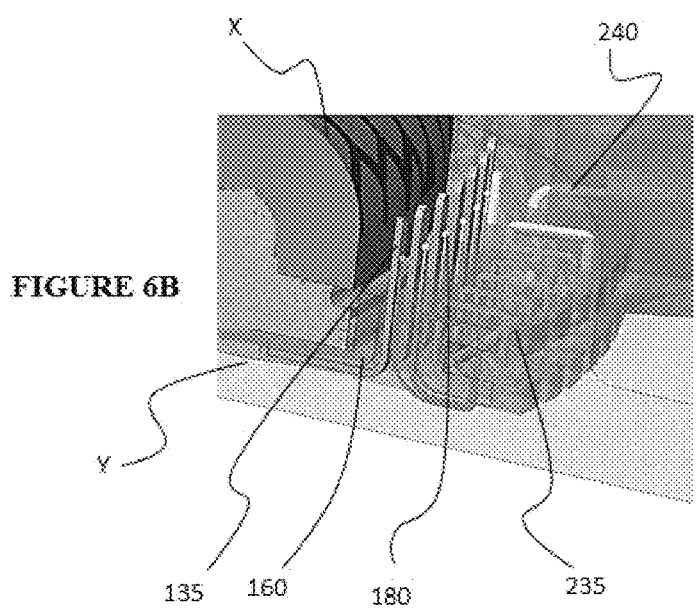
FIG. 6B illustrates an enlarged view of the wire running along periphery of the non-conductive unit according to an embodiment.

FIG. 6A illustrates a wire according to an embodiment, and FIG. 6B illustrates an enlarged view of the wire according to an embodiment. One end of the wire 125 is connected to the feedthrough connector 120 and the wire runs along a periphery 215 of the non-conductive unit 160 within the wire path (260, FIG. 5E) and another end of the wire 125 exits the wire entry/exit port 210, the plurality of electrical wires 125 are adapted to run towards the entry/exit port 210 individually or as electrically isolated bunched wires 235. The connection is made via a connection 180 at the second end section 135 of the connector 120. The connection 180 may include a weld connection.

The wires running towards the entry/exit port 210 may exit within a lead body 240. The lead body connects the electrode array (not shown) to the enclosed electronic circuit. The plurality of wires 125, exiting the entry/exit port 210, passes through the lead body 240 to bring electrical signal from the electronic circuit to the electrode array positioned within the cochlea.

Figure 7A:
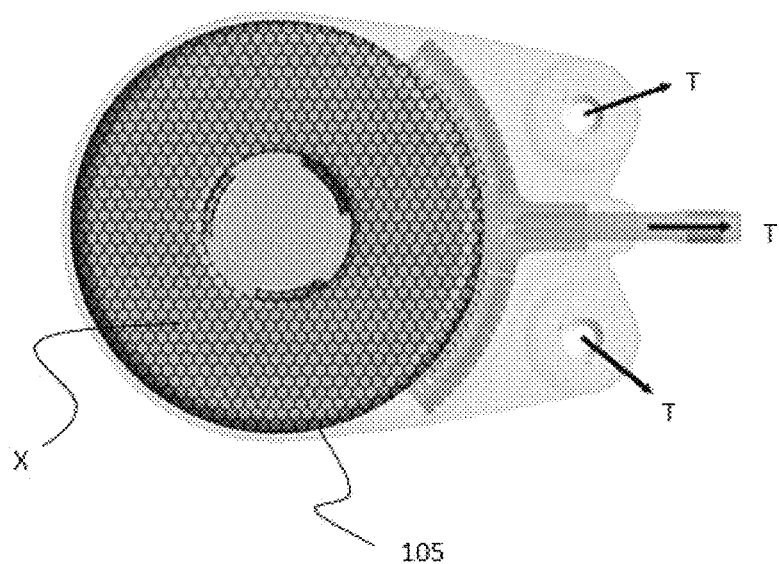
FIG. 7A illustrates directions of traction according to an embodiment.
Figure 7B:
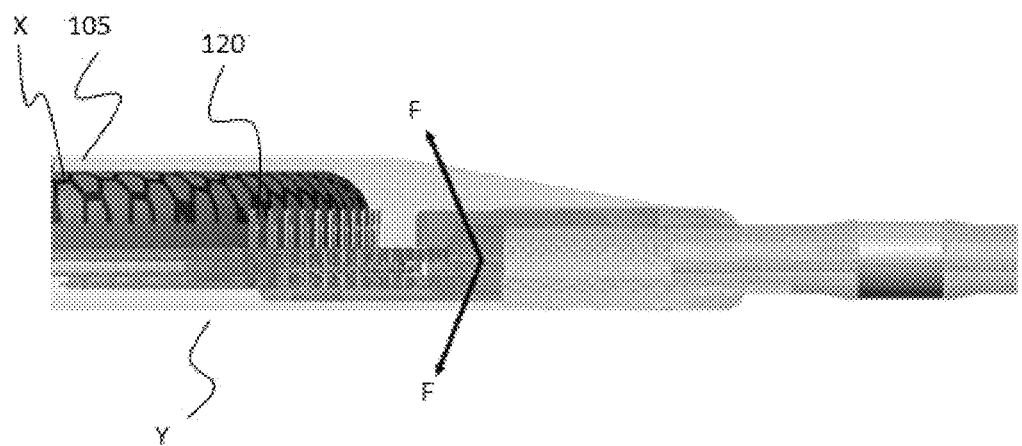
FIG. 7B illustrates directions of flexion according to an embodiment.

FIG. 7A illustrates directions of traction T according to an embodiment. Additionally, FIG. 7B illustrates direction of flexion F according to an embodiment. The extra wire length 185 protects device from traction and flexion solicitations during manufacturing, and/or use. The extra wire length avoids having a direct traction and/or flexion stress on the connections (e.g. weld connection) by transferring the stress on insulating members and the non-conductive unit. During manufacturing or device use, the soft transition area by way of connecting electrical wires, along with insulation members and the non-conductive unit allow for these components to move together. This construction also offers absorption and dissipation of the energy in the soft material without wires breakage of connection in events of impact on the housing or the connector. The implementation is thus adapted to little movements and efforts on array and eliminates or substantially reduces direct stresses on the connection, thus increasing reliability of the implant.

According to an embodiment, a method of providing terminal connections, away from a plurality of feedthrough conductors 110, for a plurality of electrical wires 125 in an implantable medical device 100 is disclosed. The method includes manufacturing a plurality of feedthrough connectors 120 that includes an arrangement of holes 230 at a first end section 130. The arrangement of holes represents an arrangement of the plurality of feedthrough conductors 110 of the device. The hole at the first end section 130 of each connector is configured to receive a corresponding feedthrough conductor 110. The manufactured plurality of feedthrough connectors 120 is positioned over a non-conductive unit 160. The plurality of feedthrough conductors 110 are received in a corresponding hole of the plurality of feedthrough connectors 120. Thereafter, one end of a plurality of electrical wires 125 are individually connected to respective second end section of one of the plurality of feedthrough connectors 120 using a connection technique. The connection technique may include a weld connection technique. Although weld connection technique to make weld connection is state but other connection techniques will be apparent to the skilled person and is within the scope of this disclosure.

The method may include one or more of the following steps:

In an embodiment, manufacturing step includes manufacturing the plurality of feedthrough connectors 120 such that the plurality of feedthrough connectors are adapted to, when positioned onto a non-conductive unit 160, include a first distance $D_{ft}$ between first end sections 130 of at least one pair of neighboring feedthrough connectors that is less than a second distance $D_{ph}$ between second end sections of the at least one pair of neighboring feedthrough connectors. Additionally or alternatively, the manufacture step may also include manufacturing the plurality of feedthrough connectors such that a first surface area $S_1$ of the first end section is less than a second surface area $S_2$ of the second end section.

Figure 8A:
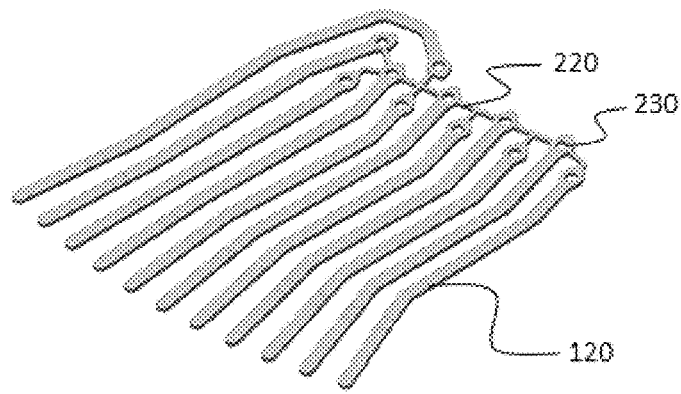
FIG. 8A illustrates a plurality of feedthrough connectors with a strip according to an embodiment.
Figure 8B:
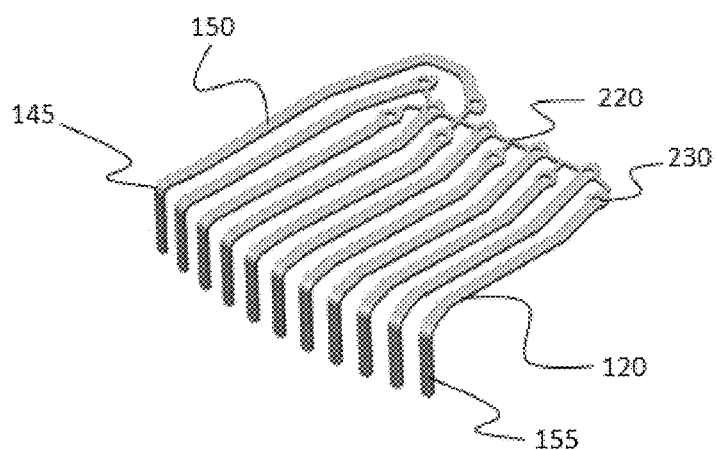
FIG. 8B illustrates a plurality of feedthrough connectors with the strip and a bend according to an embodiment.
Figure 8C:
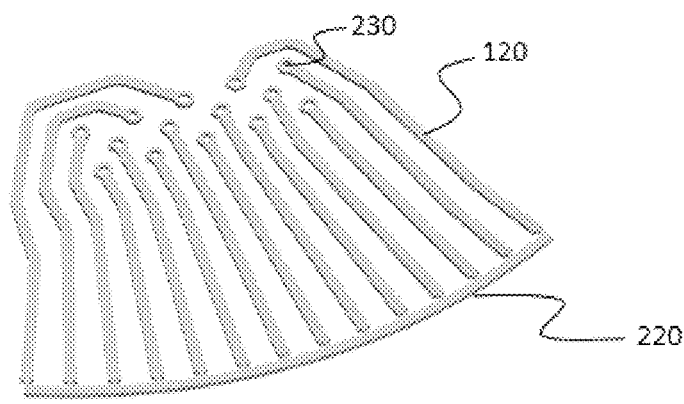
FIG. 8C illustrates a plurality of feedthrough connectors with a strip according to an embodiment.

In another embodiment, manufacturing includes manufacturing the plurality of feedthrough connectors 120 interconnected with a strip (220, FIG. 8A or FIG. 8C). The connecting strip is removed after positioning the feedthrough connectors over the non-conductive unit (See FIG. 8B).

In an embodiment, the position of the feedthrough connector over the non-conductive unit 160 includes positioning the plurality of feedthrough connectors 120 in a plurality of guiding grooves 225 of the non-conductive unit 160 such that a pair of neighboring feedthrough connectors are isolated from each other.

In another embodiment, prior to connecting the electrical wires to respective second end section 135, an extra wire length 185 in form of at least one wire loop in immediate proximity to a connection site (e.g. welding site) at the second end section 135 is provided. The extra wire length 185 may also be sandwiched between a pair of insulating members 190.

In yet another embodiment, prior to connecting the electrical wires 125 to respective second end section 135, the plurality of feedthrough connectors 120 are bent around the peripheral edge 170 of the non-conductive unit 160. The bend 145 defines a primary section 150 and a secondary section 155 for each of the plurality of feedthrough connectors 120 and the connection 180 (for example the weld connection) is made at the secondary section 155.

In an embodiment, the strip (220, FIG. 8A, FIG. 8B and FIG. C) may be removed either before or after making the bend 145. The latter is shown in FIG. 8B.

In an embodiment, following the connection of the electrical wires 125 to respective second end section 135, a peripheral cover 195 is fixed onto the non-conductive unit 160. The peripheral cover 195 in co-operation with the non-conductive unit 160 defines a wire entry/exit port 210 when the peripheral cover 195 is in an assembled position. Other end of the plurality of electrical wires are then drawn out of the entry/exit port.

In different combinable embodiments, the method is adapted to include features of the device described in preceding paragraphs.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

We claim:

1. An implantable medical device comprising
a sealed housing enclosing an electronic circuitry;
a plurality of feedthrough conductors, each conductor of the plurality of feedthrough conductors comprising a proximal end part connected to the enclosed electronic circuitry and a distal end part available external to the housing; and
a plurality of spatially separated feedthrough connectors configured to provide terminal connections, away from the plurality of feedthrough conductors, for a plurality of electrical wires, wherein
each connector of the plurality of spatially separated feedthrough connectors comprises
a first end section external to the housing, which is adapted to be connected with the distal end part of a feedthrough conductor of the plurality of feedthrough conductors, and
a second end section external to the housing, which is adapted to be connected with one of the plurality of electrical wires,
wherein at least one wire of the plurality of electrical wires comprises an extra wire length in form of at least one wire loop in immediate proximity to a connection site at the second end section.

2. The device according to claim 1, wherein the plurality of spatially separated feedthrough connectors, when positioned onto a non-conductive unit, are configured such that a first distance $D_{ft}$ between first end sections of at least one pair of neighboring feedthrough connectors is less than a second distance $D_{ph}$ between second end sections of the at least one pair of neighboring feedthrough connectors.

3. The device according to claim 1, wherein a first surface area $S_1$ of the first end section is less than a second surface area $S_2$ of the second end section.

4. An implantable medical device comprising
a sealed housing enclosing an electronic circuitry;
a plurality of feedthrough conductors, each conductor of the plurality of feedthrough conductors comprising a proximal end part connected to the enclosed electronic circuitry, and a distal end part available external to the housing; and
a plurality of spatially separated feedthrough connectors configured to provide terminal connections, away from the plurality of feedthrough conductors, for a plurality of electrical wires,
wherein each connector of the plurality of spatially separated feedthrough connectors comprises a first end section adapted to be connected with the distal end part of a feedthrough conductor of the plurality of feedthrough conductors, and a second end section adapted to be connected with one of the plurality of electrical wires, and
wherein each connector of the plurality of spatially separated feedthrough connectors comprises a bend, around a peripheral edge of a non-conductive unit, between the first end section and the second end section, the bend defining a primary section comprising the first end section and a secondary section comprising the second end section of the feedthrough connector.

5. The device according to claim 4, wherein the primary section of at least one connector of the plurality of feedthrough connectors includes at least one turn along a length of the primary section.

6. The device according to claim 2, wherein the non-conductive unit rests on the housing, the non-conductive unit being adapted to support the plurality of spatially separated feedthrough connectors and to isolate a pair of neighboring feedthrough connectors of the plurality of spatially separated feedthrough connectors.

7. The device according to claim 4, wherein the non-conductive unit comprises a base on which at least a part of the primary section rests, the peripheral edge along which the bend rests, and a side section to which the secondary section abuts.

8. The device according to claim 2, wherein the non-conductive unit comprises a plurality of guiding grooves, each groove of the plurality of guiding groove being adapted to receive the connector of the plurality of spatially separated feedthrough connectors and isolate a pair of neighboring feedthrough connectors of the plurality of spatially separated feedthrough connectors.

9. The device according to claim 1, further comprising a hole at the first end section of the connector, the hole being adapted to receive the feedthrough conductor.

10. The device according to claim 1, further comprising a connection to connect one end of the wire to the second end section of the feedthrough connector, the connection being distal from the plurality of feedthrough conductors.

11. The device according to claim 10, further comprising a pair of insulating members adapted to sandwich the extra wire length therebetween, wherein the insulating member extends beyond a peripheral edge of a non-conductive unit.

12. The device according to claim 11, wherein the insulating member is an integral part of the non-conductive unit or adapted to be removably attached with the non-conductive unit.

13. The device according to claim 2, further comprising a peripheral cover adapted to fix to the non-conductive unit.

14. The device according to claim 13, wherein the peripheral cover comprising a cover section that is configured to co-operate with a unit section of the non-conductive unit to define a wire path and/or a wire entry/exit port when the peripheral cover is in an assembled position.

15. The device according to claim 1, wherein one end of the wire is connected to the feedthrough connector and the wire runs along a periphery of the non-conductive unit within the wire path and another end of the wire exits the wire entry/exit port, the plurality of electrical wires are adapted to run towards exit the entry/exit port individually or as electrically isolated bunched wires.

16. The device according to claim 1, wherein the implantable medical device is an implantable part of a cochlear implant system.

17. A cochlear implant comprising the implantable medical device according to claim 1.

\* \* \* \* \*